United States Patent [19]

Jessup

[11] Patent Number: 5,500,063
[45] Date of Patent: Mar. 19, 1996

[54] METHOD OF JOINING AN ELASTIC BAND TO A CONTINUOUSLY MOVING PARTIALLY ELASTIC SUBSTRATE

[75] Inventor: James L. Jessup, Appleton, Wis.

[73] Assignee: Kimberly-Clark Corporation, Neenah, Wis.

[21] Appl. No.: 267,272

[22] Filed: Jun. 28, 1994

[51] Int. Cl.$^6$ .................................................. B32B 31/04
[52] U.S. Cl. ........................... 156/85; 156/160; 156/163; 156/227; 156/229; 156/264; 156/308.4; 156/496; 604/385.1; 604/385.2
[58] Field of Search ................................ 156/163, 164, 156/84, 85, 229, 496, 264, 227, 308.4; 604/358, 385.1, 385.2

[56] References Cited

U.S. PATENT DOCUMENTS

| | | |
|---|---|---|
| 1,544,312 | 6/1925 | Gray . |
| 2,976,199 | 3/1961 | Rand . |
| 3,604,015 | 9/1971 | Dove . |
| 3,966,527 | 6/1976 | Gros . |
| 4,033,801 | 7/1977 | Gros . |
| 4,450,026 | 5/1984 | Peniak et al. ........................... 156/164 |
| 4,486,192 | 12/1984 | Sigl . |
| 4,525,407 | 6/1985 | Ness . |
| 4,543,154 | 9/1985 | Reiter . |
| 4,563,185 | 1/1986 | Reiter . |
| 4,582,550 | 4/1986 | Sigl ..................................... 156/85 X |
| 4,641,381 | 2/1987 | Heran et al. . |
| 4,652,487 | 3/1987 | Morman . |
| 4,657,802 | 4/1987 | Morman . |
| 4,663,220 | 5/1987 | Wisneski et al. . |
| 4,720,415 | 1/1988 | Vander Wielen et al. . |
| 4,808,252 | 2/1989 | Lash . |
| 4,861,652 | 8/1989 | Lippert et al. . |
| 4,883,549 | 11/1989 | Frost et al. ............................. 156/161 |
| 4,916,005 | 4/1990 | Lippert et al. . |
| 4,925,520 | 5/1990 | Beaudoin et al. . |
| 4,940,464 | 7/1990 | Van Gompel et al. .................. 604/396 |

FOREIGN PATENT DOCUMENTS

| | | |
|---|---|---|
| 0119827 | 9/1984 | European Pat. Off. . |
| 217032 | 4/1987 | European Pat. Off. . |
| WO9409736 | 5/1994 | WIPO . |

OTHER PUBLICATIONS

Pending U.S. application Ser. No. 096,654.
Pending U.S. application Ser. No. 043,132.

Primary Examiner—Jeff H. Aftergut
Assistant Examiner—David W. Reed
Attorney, Agent, or Firm—Douglas L. Miller

[57] ABSTRACT

A method is provided for joining an elastic band to a continuously moving, partially elastic substrate. The method includes temporarily inhibiting portions of the elastic band and then positioning the band on the substrate. The substrate includes elastic and non-elastic segments, and the band is positioned so that an elastic portion of the band is on an elastic segment of the substrate and the temporarily inhibited portion of the band is on the non-elastic segment of the substrate. The band and substrate are then joined together, and the temporarily inhibited portion is activated to gather the non-elastic segment.

19 Claims, 6 Drawing Sheets

5,500,063

METHOD OF JOINING AN ELASTIC BAND TO A CONTINUOUSLY MOVING PARTIALLY ELASTIC SUBSTRATE

BACKGROUND OF THE INVENTION

The present invention relates to methods of joining a length of material to a continuously moving substrate, and more particularly to methods of joining an elastic material to a continuously moving, partially elastic substrate.

There are, today, an increasing number of products incorporating some type of elastic material to provide stretch to the products. Examples of these products incorporating elastic material include general wearing apparel, athletic apparel, and specialized apparel, such as surgical gowns, hospital gowns, and other medically-related apparel.

Other examples of different types of product include vehicle protective covers, camping-related materials such as tents for example, or the like.

Still other examples include disposable absorbent articles, such as baby diapers, children's training pants, adult incontinence products, feminine care products, or the like.

One of the intended purposes of incorporating elastic materials into these products is to keep the products secure or snug in their proper positions. For example, certain designs of general wearing apparel may require a tight fit so as to have a uniquely fashionable look. Athletic apparel needs to be maintained in place during aggressive physical activity required in some sports. Surgical and hospital apparel needs to fit properly for sanitary and health purposes.

Similarly, vehicle protective covers and camping-related materials desirably should withstand the effects of high or gusty winds and other severe weather conditions. A secure fit, whether over a vehicle or a tent frame, for example, can help weather these types of outdoor conditions.

In the area of disposable absorbent articles, a proper fit, both before and after an accident or insult, is important in preventing body waste material from leaking out of the product onto the wearer.

One problem associated with incorporating an elastic material into a product is the elastic material's potentially premature contracting during the manufacturing process. Any premature gathering of the product can cause subsequent processing steps to be off-line or unregistered, thereby resulting in material waste and increased costs in manufacture. One specific example of this is a training pant intended to be worn during the potty-training stage of young children. One style of training pant has elastic side panels that fit against the hips of the child, and discrete front and back elastic waist strips adjacent the waist opening. The waist strips are applied during the manufacturing process, and generally at a different point or time in the process from the elastic side panels. The individual training pants are folded and bonded along portions of side edges to form a waist opening and a pair of leg openings. If, for example, the elastic waist strips prematurely gather, the subsequent folding and bonding steps will not be properly performed, thereby resulting in irregular products that must be culled and disposed of.

Another problem associated with incorporating an elastic material into a product is the difficulty of properly maintaining a desired elasticity in the product during both the joining of the elastic material and subsequent handling steps. If the desired elasticity cannot be maintained, the product may not fit properly, and ultimately result in unsatisfactory performance.

A further problem exists when incorporating an elastic material into a partially elastic product, and particularly during the manufacturing process when the extensible direction of the elastic material is different from the direction of run of a continuous, partially elastic substrate, from which multiple individual products will be made. This problem is complicated when the partially elastic substrate is extensible in the same direction as the elastic material and it is desired that the joining of the elastic material should not substantially inhibit the desired elasticity of the partially elastic substrate. For example, the continuously running length of partially elastic substrate, from which some type of apparel is to be made, can have elastic portions that extend in a direction transverse to the direction the substrate is being run. A problem arises here when an elastic material, such as an elastic band for example, is to be joined to the partially elastic substrate such that the direction of extension of the elastic band also is transverse to the direction the partially elastic substrate is being run.

Yet another problem is the accurate joining of an elastic material in today's high speed manufacturing environment. Some products are manufactured at speeds of about 200–800 products per minute. Since the materials that form the product are provided at relatively high speeds, problems in material handling must be avoided if the manufacturing process is to be fast, continuous, and economical. Otherwise, there will be unacceptable and costly downtime in the manufacturing process to correct these problems.

In view of the above, there is a need today for a process for joining an elastic material to a continuously moving, partially elastic substrate.

In one form of the present invention there is provided a method of joining a plurality of elastic bands to a continuously moving, partially elastic substrate comprising the steps of (1) continuously moving in a first direction a substrate including a plurality of non-elastic segments and a plurality of elastic segments that are extensible in a second direction different from the first direction, (2) providing a supply of an elastic band and tensioning the elastic band, (3) temporarily inhibiting portions of the elastic band, (4) cutting the elastic band into individual elastic bands so that each individual elastic band includes at least one temporarily inhibited portion and at least one elastic portion, (5) sequentially orienting each individual elastic band so that it is extensible in substantially the same direction as the elastic segments of the continuously moving substrate, (6) positioning each individual elastic band over the continuously moving substrate so that each elastic portion of the band is over one of the elastic segments of the substrate, and each temporarily inhibited portion of the band is over one of the non-elastic segments of the substrate, and (7) joining each individual elastic band to the continuously moving substrate.

In another form of the present invention there is provided a method of joining a plurality of elastic bands to a continuously moving, partially elastic composite structure comprising the steps of (1) continuously moving in a first direction a composite structure including a continuous topsheet, a continuous backsheet, a plurality of spaced apart absorbent structures between the continuous topsheet and continuous backsheet, and a plurality of spaced apart elastic side members on opposite sides of the continuous backsheet and being extensible in a second direction different from the first direction, (2) providing a supply of an elastic band and tensioning the elastic band, (3) temporarily inhibiting portions of the elastic band, (4) cutting the elastic band into individual elastic bands so that each individual elastic band includes a pair of elastic portions and a temporarily inhibited portion therebetween, (5) sequentially orienting each individual elastic band so that it is extensible in substantially the same direction as the elastic side members, (6) positioning each individual elastic band over the continuously moving composite structure so that the temporarily inhibited portion of the band is over the backsheet, and a pair of elastic portions are over a respective pair of opposite spaced apart elastic side members, and (7) joining each individual elastic band to the continuously moving composite structure.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein.

DEFINITIONS

Figure 1:
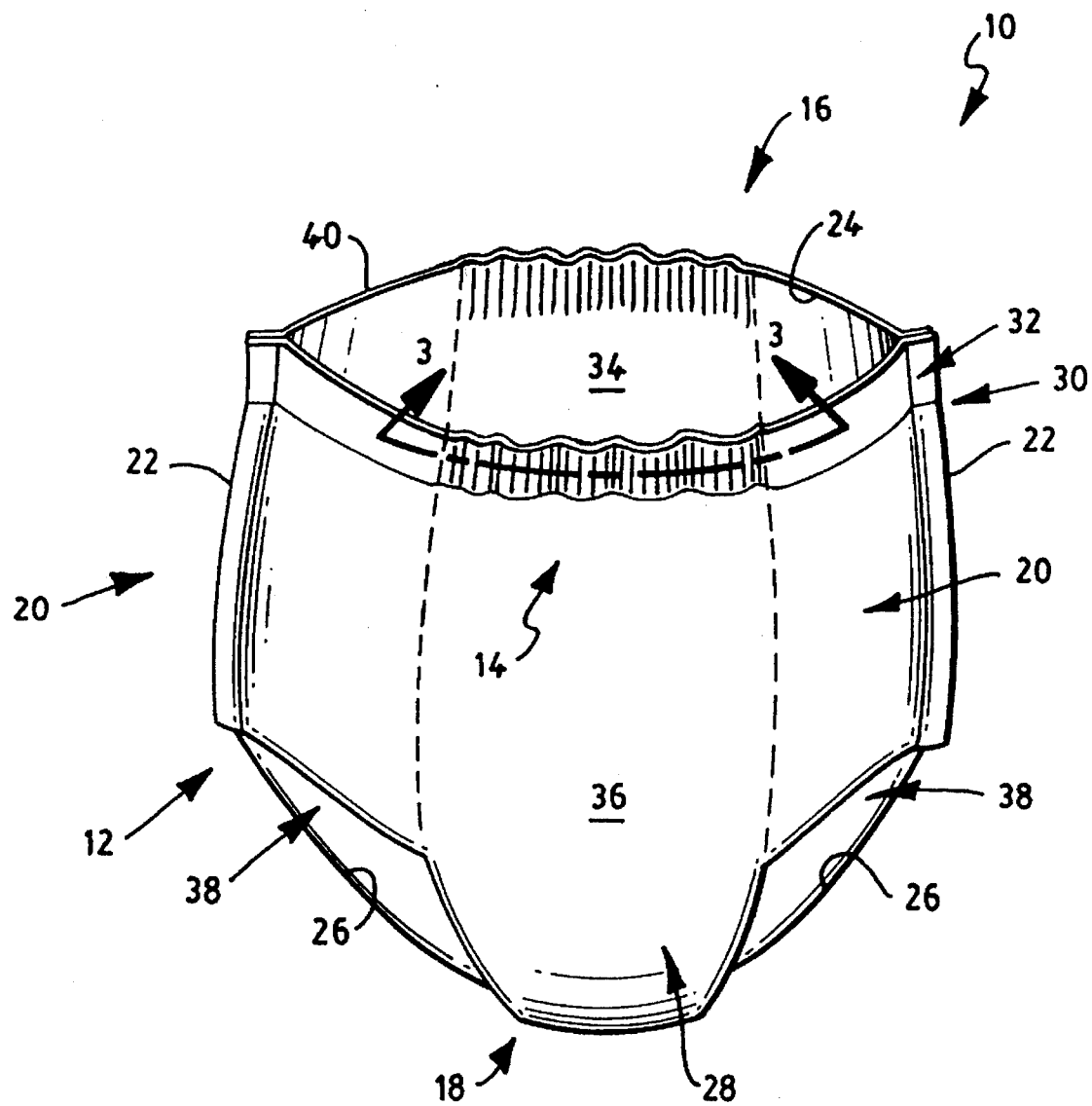
FIG. 1 illustrates a front perspective view of one type of a disposable, elastic, absorbent garment made in accordance with the principles of the present invention.

Each of the following terms used herein include the following meaning:

"Composite elastic material" or "composite elastic web" means a multi-layered material having at least one elastic layer joined to at least one gatherable layer at least at two locations wherein the gatherable layer is gathered between the locations where it is joined to the elastic layer. A composite elastic material may be stretched to the extent that the non-elastic material gathered between the bond locations allows the elastic material to extend. This type of composite elastic material is disclosed, for example, by Vander Wielen et al., U.S. Pat. No. 4,720,415 issued Jan. 19, 1988, the content of which is incorporated by reference herein.

"Continuous" means that the described structure is a closed-loop structure. The continuous structure may be unitary, i.e., a one-piece structure, or may be made up of individual elements suitably joined together to form a closed-loop.

"Disposable" means that the described garment is designed to be used until soiled, either by urination, defecation, or otherwise, and then discarded, rather than being washed and used again.

"Elastic", "elasticity", "elasticized", and the like, refers to a material or composite material that tends to recover its original size and shape after removal of the force causing the deformation, and is expressed as a percent.

"Elongation" means the ratio of the extension of a material to the length of the material prior to the extension (expressed in percent), as represented by the following:

$$\frac{\text{Extended Length} - \text{Original Length}}{\text{Original Length}} \times 100.$$

"Extension", "extend", "extended", or variations thereof, refers to the change in length of a material due to stretching (expressed in units of length).

"Extensible" means that the described material can be increased in length.

"Finished garment" means that the garment has been suitably manufactured for its intended use.

"Join", "joining", "joined", or variations thereof, when used in describing the relationship between two or more elements, means that the elements can be connected together in any suitable manner, such as by heat sealing, ultrasonic bonding, thermal bonding, by adhesives, stitching, or the like. Further, the elements can be joined directly together, or may have one or more elements interposed between them, all of which are connected together.

"Operatively elastically joined" describes the joining of an elastic member to a non-elastic member such that the two joined members exhibit elasticity.

"Pant body" refers to a garment that has a waist opening and a pair of leg openings, similar to shorts, swim wear, or the like. The described garment may or may not have a manually tearable side seam.

"Recover", "recovering", or variations thereof, refers to a contraction of an extended material upon termination or removal of a biasing force, or upon suitably treating the material after it has been temporarily inhibited.

"Substrate" means a layer which may be, for example, a film, woven web, or nonwoven web; or a composite structure comprising, for example, a topsheet, a backsheet, and an absorbent medium therebetween.

"Temporarily inhibit" means to delay the total recovery of an extended elastic substrate or composite elastic material. The delay may be imparted by compressing the extended elastic substrate, or by compressing the composite elastic material so that the elastic and gatherable layers are temporarily joined. Partial recovery of a temporarily inhibited elastic substrate or composite elastic material may occur immediately after the force is removed, but total recovery of such a temporarily inhibited elastic substrate or composite elastic material will require more time than the total recovery of the same material which has not been temporarily inhibited. For example, total recovery of an extended elastic substrate or composite elastic material that has not been temporarily inhibited may be instantaneous, whereas the total recovery of a temporarily inhibited elastic substrate or composite elastic material may take, for example, from about 5 to about 60 seconds.

"Total recovery" or variations thereof, refers to a material recovering to generally within about 20 percent of its relaxed, pre-extended dimensions.

DETAILED DESCRIPTION

The present invention can be utilized to manufacture any type of product that is partially elastic, and to which is to be joined an elastic material or band. The present invention is especially useful when the individual products are being manufactured from a continuously moving partially elastic substrate having elastic portions extensible in a direction different from the direction of travel of the continuously moving substrate, and to which is to be joined an elastic material or band that stretches in the same direction as the elastic portions of the continuously moving substrate. Some of the products contemplated to be manufactured in accordance with the principles of the present invention include apparel, vehicle protective covers, camping-related materials, disposable absorbent articles, or the like. The description of a method of the present invention will be made with reference to one specific product, but it should be understood that the present invention is adaptable to manufacture other and differing types of products as described above.

Referring primarily to FIG. 1, there is illustrated a partially elastic composite structure in the form of a disposable absorbent garment 10. The phrase "partially elastic composite structure" includes a garment or product comprising two or more structural elements, such as two or more layers of material, and having portions thereof that are elastic. Disposable absorbent garment 10 includes a pant body 12 comprising a front section 14, a back section 16, a crotch section 18, elastic side sections 20, seams 22, a continuous waist opening 24, and a pair of continuous leg openings 26. Each elastic side section 20 includes a front elastic side member 68 (FIG. 5) and a back elastic side member 70, which are joined together at a respective seam 22. Garment 10 further includes a continuous waistborder 30 (FIGS. 1–2), continuous leg borders 38, and a continuous waistband 32. Continuous waistband 32 comprises a front waistband member 64 (FIG. 5) and a back waistband member 66. Continuous waistborder 30 comprises a front waistborder section 42 (FIGS. 4, 5) having a front edge 44 and a back waistborder section 46 having a back edge 48. An absorbent structure 28 is suitably incorporated into garment 10 at least at crotch section 18 thereof.

Pant body 12 includes a topsheet 34 (FIG. 4) and a backsheet 36, which are desirably coincident with one another, although not a requirement of the present invention. Backsheet 36 (FIG. 5) includes a pair of front outer edges 50, front inner edges 52, innermost edges 54, back sloping edges 56, and back outer edges 58.

Figure 4:
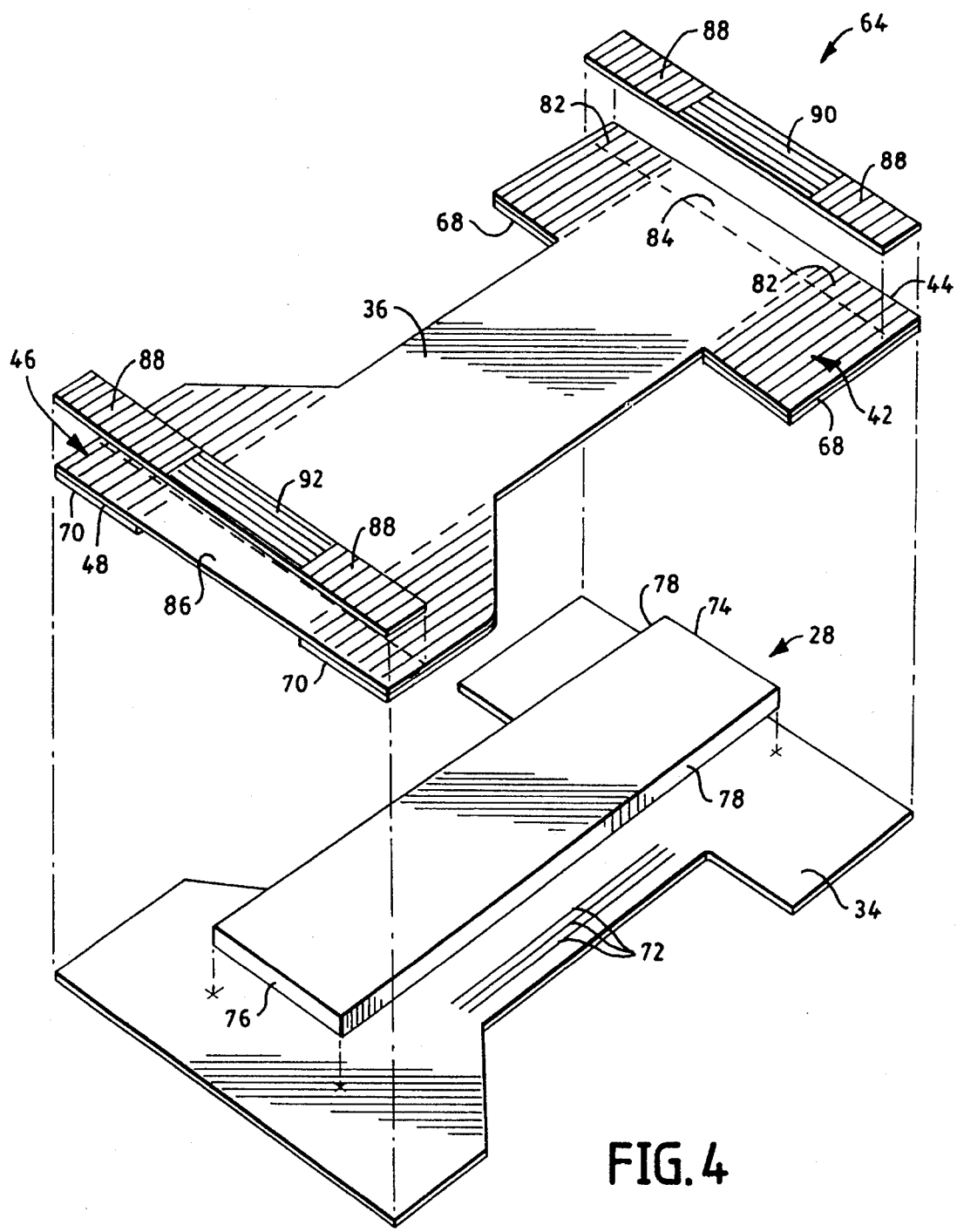
FIG. 4 illustrates an exploded, perspective view of the garment in FIG. 1 in a partially disassembled, extended flat state.
Figure 5:
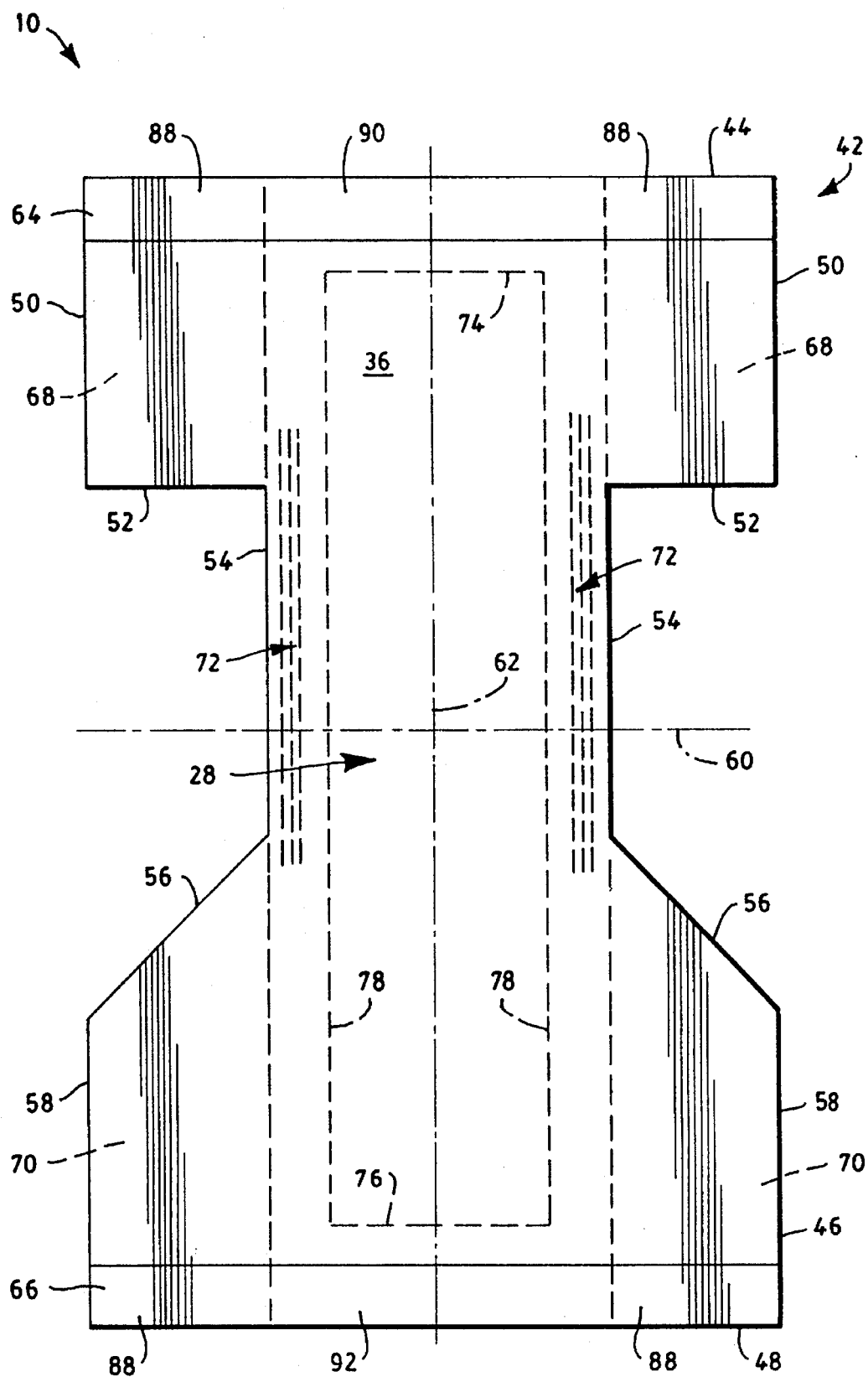
FIG. 5 illustrates a top plan view of the garment in FIG. 1 in a partially finished, extended flat state.

Front waistband member 64 (FIGS. 4, 5) is suitably joined to front waistborder section 42, and back waistband member 66 is suitably joined to back waistborder section 46. Front and back waistborder sections 42, 46 desirably have respective lengths substantially corresponding to the respective lengths of front and back waistband members 64, 66, and widths substantially corresponding to the respective widths of front and back waistband members 64, 66; length being measured along a line generally parallel to transverse centerline 60 (FIG. 5) and width being measured along a line generally parallel to longitudinal centerline 62. A desired width range of waistband members 64, 66 is between about 1 centimeter to about 8 centimeters, and a more desired range is between about 2 centimeters to about 4 centimeters. In the case where, for example, one or both of the waistband members 64, 66 have some other geometric shape, i.e., not an elongate rectangular shape as illustrated in FIGS. 4 and 5, each waistborder section 42, 46 desirably would have substantially the same geometric shape as its respective waistband member 64, 66. Both front and back waistband members 64, 66 are elastically extensible at least in a direction generally parallel to transverse centerline 60.

With reference primarily to FIGS. 1 and 5, when garment 10 is folded along a transverse fold-line, which is generally parallel to transverse centerline 60, and pairs of aligned front and back outer edges 50, 58 are joined together to form seams 22, the following construction is accomplished: (i) front waistborder section 42 and back waistborder section 46 form or define continuous waistborder 30; (ii) front waistband member 64 and back waistband member 66 form or define continuous waistband 32; (iii) a front inner edge 52, an innermost edge 54, and a back sloping edge 56 form or define a respective leg opening 26; (iv) and a front elasticized side member 8 and a back elasticized side member 70 form or define a respective elasticized side section 20.

Garment 10 also comprises a pair of leg elastic members 72 (FIG. 5) that are suitably joined, for example, between topsheet 34 and backsheet 36 (FIG. 1).

Absorbent structure 28 (FIGS. 4, 5) comprises front absorbent edge 4, back absorbent edge 76, and absorbent side edges 78. As illustrated in FIG. 5, front absorbent edge 74 and back absorbent edge 76 are respectively inboard of front waistband member 64 and back waistband member 66. Similarly, absorbent side edges 78 are inboard of respective leg elastic members 72. By "inboard" is meant that absorbent front edge 74, for example, is closer to transverse centerline 60 than front waistband member 64, and absorbent side edges 78 are closer to longitudinal centerline 62 than leg elastic members 72.

When garment 10 is properly fitted on the wearer, topsheet 34 faces toward the body of the wearer, and may or may not be the layer that directly contacts the skin. Topsheet 34 can be a liquid permeable, elastic or non-elastic, substantially hydrophobic material, such as a spunbonded web of synthetic polymer filaments. Topsheet 34 can also be a meltblown web or a bonded carded web of synthetic polymer filaments. Suitable synthetic polymers include, for example, polyethylene, polypropylene, and polyesters. Topsheet 34 has a pore size that readily allows the passage therethrough of liquids, such as urine and other body exudates. If desired, topsheet 34 can be treated with surfactants to selectively adjust its degree of wettability, and can also be selectively embossed or perforated with discrete slits or holes extending therethrough. Suitable topsheet materials can have a basis weight between about 10 grams per square meter (gsm) to about 26 gsm, and a thickness between about 0.013 centimeters to about 0.064 centimeters. The thickness of the topsheet material can be determined by employing an Ames Bulk Test (ASTM D-1777) performed at a restraining pressure of 0.2 psi (1.38 kPa).

Backsheet 36, which may or may not be the outermost layer of garment 10, can be liquid permeable or liquid impermeable, and may or may not have breathability, i.e., be vapor permeable. A suitable liquid permeable backsheet 36 is a nonwoven bicomponent web having a basis weight between about 15 gsm to about 50 gsm. The nonwoven bicomponent web may be a spunbond bicomponent web, or a bonded carded bicomponent web. Suitable bicomponent fibers are a wettable, polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, or end-to-end. Another suitable liquid permeable material is a liquid permeable spunbond polypropylene nonwoven web having a basis weight between about 15 gsm to about 50 gsm.

A suitable liquid impermeable backsheet 36 is a 0.0015 centimeter polyethylene film from Edison Plastics Company, South Plainfield, N.J. Backsheet 36 can also be a two-ply laminate, in which the innermost layer can be the above-described liquid impermeable film or any other suitable liquid impermeable layer, and the outermost layer can be the above-described liquid permeable spunbond polypropylene nonwoven web or any other suitable liquid permeable layer. Backsheet 36 desirably has a thickness within the range of about 0.0013 to about 0.0051 centimeters.

Absorbent structure 28 can comprise any suitable absorbent material, natural or synthetic, or a combination thereof, along with superabsorbent material. The absorbent material of which absorbent structure 28 is made may also be encased in a tissue wrap (not shown) in order to maintain the integrity of the absorbent material comprising absorbent structure 28. Suitable superabsorbent materials are available from various vendors, such as Dow Chemical Company, Hoechst-Celanese Corporation, and Allied Colloids, Inc. A suitable natural absorbent material is a wood pulp fluff identified by the trade designation CR1654 from Kimberly-Clark Corporation, Neenah, Wis. One specific absorbent structure 28 that can be suitably used in garment 10 is described in U.S. patent application Ser. No. 08/096,654 filed Jul. 22, 1993, inventors Hanson et al., which is assigned to the assignee of this application, the content of which is incorporated by reference herein.

The construction of garment 10 can be accomplished in any suitable manner. For example, the structural elements can be joined together in any manner, such as by heat sealing or ultrasonic bonding, or by adhering the elements together with a suitable adhesive. Suitable adhesives can be obtained from Findley Adhesives, Inc., Wauwatosa, Wis., and can be applied in any manner, such as by spraying, slot-coat extrusion, printing, or the like. The applied adhesive can be in any desired configuration, such as continuous or discontinuous beads, continuous or discontinuous swirls, meltblown patterns, spray patterns, or the like.

Referring to FIGS. 1–5, front elasticized side members 68 (FIG. 5) can have the same or different geometry from back elasticized side members 70. Each front elastic side member 68 and each back elastic side member 70 comprises an elastic layer 80 (FIG. 3) sandwiched between topsheet 34 and backsheet 36. Elastic layer 80 can be any suitable elastic material, such as any of the materials in the KRATON® G and KRATON® D series of The Shell Chemical Company. Elastic layer 80 can be a film, nonwoven web, or ribbons or threads of synthetic or natural rubber arranged, for example, in a spaced, parallel manner. Similar to front and back waistband members 64, 66, front and back elasticized side members 68, 70 are elastically extensible at least in a direction generally parallel to transverse centerline 60.

Each elastic layer 80 is operatively elastically joined to a portion of either topsheet 34 or backsheet 36, preferably to portions of both topsheet 34 and backsheet 36, in order to provide elasticity to those portions. One example of this is disclosed in U.S. patent application Ser. No. 08/043,132 filed Mar. 25, 1993, inventor Van Gompel et al., the content of which is incorporated by reference herein. Another example of providing elastic side sections 20 is described in U.S. Pat. No. 4,940,464, issued Jul. 10, 1990, to inventor Van Gompel et al., the content of which is incorporated by reference herein.

Still other examples of elastic materials and composites are described in U.S. Pat. No. 4,720,415, issued Jan. 19, 1988, to Vander Wielen et al.; U.S. Pat. No. 4,657,802, issued Apr. 14, 1987, to Morman; and U.S. Pat. No. 4,652,487, issued Mar. 24, 1987, to Morman; the contents of these three patents being incorporated by reference herein.

Each elastic side section 20 in disposable absorbent garment 10 (FIG. 1) can have an elasticity between about 50% to about 250%, desirably an elasticity between about 75% to about 200%, and more desirably an elasticity between about 100% to about 150%.

Figure 2:
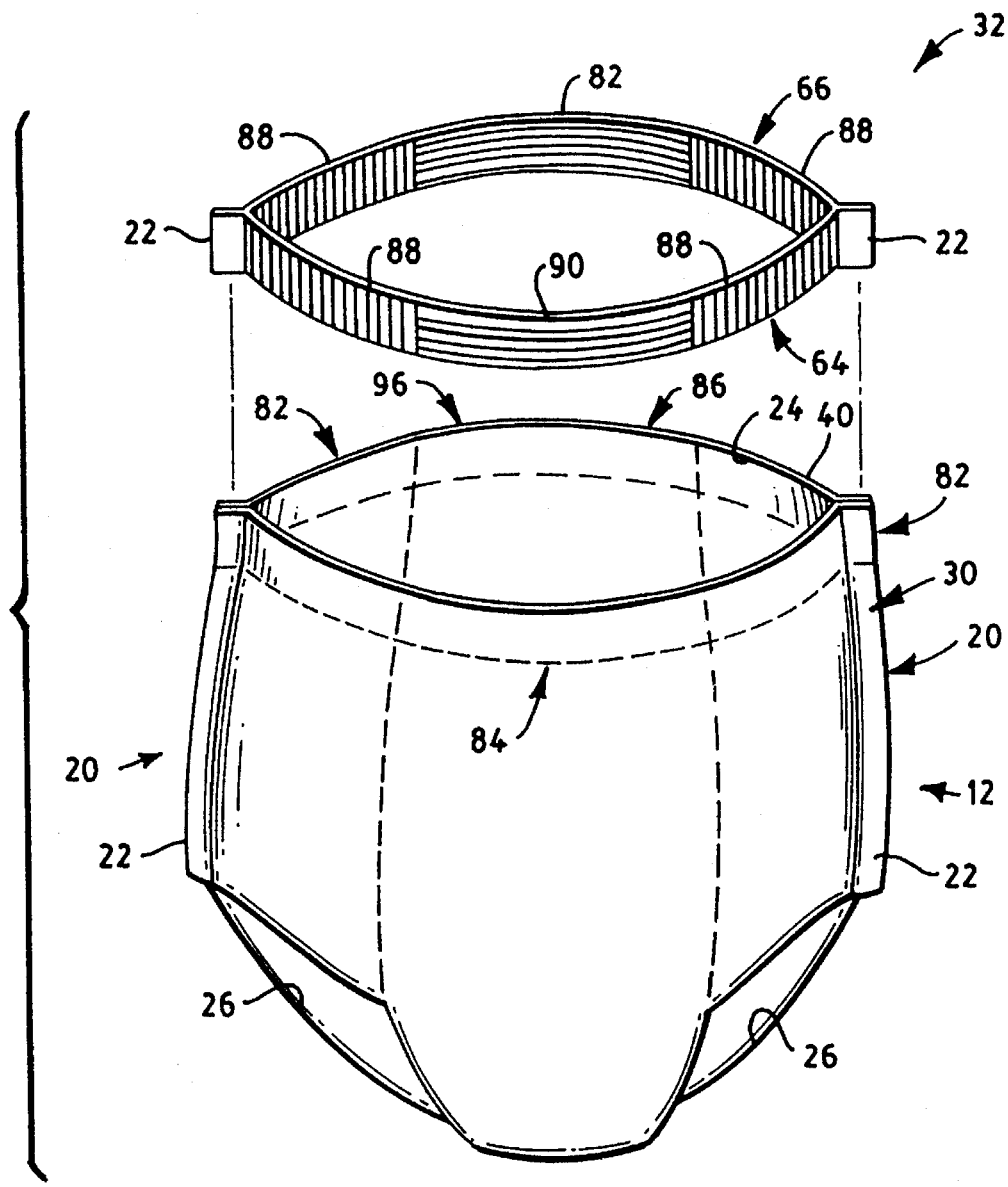
FIG. 2 illustrates a partially exploded view of FIG. 1 with a continuous, elastic waistband separated from the garment.
Figure 3:
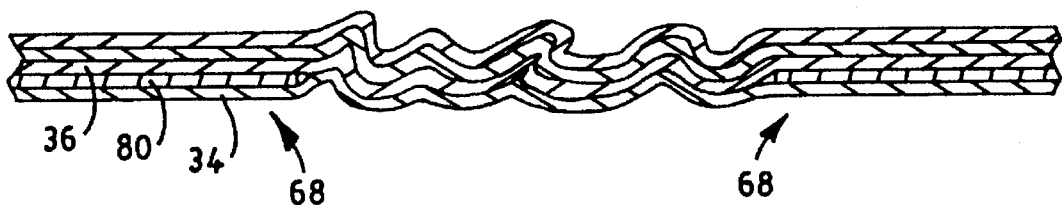
FIG. 3 illustrates a cross-sectional view of FIG. 1 taken along line 3—3 and viewed in the direction of the arrows.

Referring primarily to FIGS. 2, 4–5, continuous waistborder 30 (FIG. 2) comprises oppositely disposed elastic side segments 82, non-elastic front segment 84, and non-elastic back segment 86. Each elastic side segment 82 includes a portion of a respective elastic side section 20. Non-elastic front segment 84 and non-elastic back segment 86 include portions of topsheet 34 and backsheet 36. Thus, continuous waistborder 30 (FIG. 2) is partially elastic due to elastic side segments 82. Elastic side segments 82 are elastically extensible at least in a direction generally parallel to transverse centerline 60.

Continuous waistband 32 can be an elastomeric, cloth-like, nonwoven fibrous material, such as an elastomeric stretch bonded laminate web or an elastomeric meltblown web. By proper selection of materials, continuous waistband 32 can be rendered temporarily elastically inhibited, such as by compression. Once temporarily elastically inhibited, the elastic material, of which waistband 32 is comprised, can be activated, such as by treating with heat, to recover to a state of elasticity.

In one specific embodiment, waistband 32 comprises an elastomeric nonwoven fibrous web that is substantially vapor-permeable. Examples of suitable elastomeric nonwoven fibrous webs are described in U.S. Pat. No. 4,663,220, issued May 5, 1987, to Wisneski et al., which is incorporated by reference herein. Examples of composite fabrics comprising at least one layer of nonwoven textile fabric joined to a fibrous elastic layer are described in European Patent Application EP 0 217 032 published on Apr. 8, 1987, inventors J. Taylor et al., which is incorporated by reference herein. The composite nonwoven fabrics are commonly referred to as stretch bonded laminates.

In another embodiment, waistband 32 comprises a composite elastomeric web comprising individual, discrete strips or strands of elastomeric material secured to one or more nonwoven fibrous layers. Such a composite elastomeric web may, for example, comprise an elastomeric meltblown material arranged i n a selected pattern of strips and suitably sandwiched and joined between two layers of nonwoven fibrous material. This material, as well as others, is described in U.S. Pat. No. 4,861,652 issued Aug. 29, 1989, which is incorporated by reference herein. Still other useful composite elastic materials are described in U.S. No. 4,883,549, issued Nov. 28, 1989, which is incorporated by reference herein.

One of the innovative features of the present invention is selectively providing portions of an elastic material, such as continuous waistband 32 (FIGS. 1–2), with different elasticities as determined by, for example, the elasticity of elastic side sections 20 and the desired elasticity to be provided to non-elastic front segment 84 and/or non-elastic back segment 86.

Another innovative feature of the present invention is the provision of an elastic band or material along a partially elastic substrate so that the elastic band does not substantially restrict or diminish the elasticity of that portion of the substrate that is elastic, and to provide a desired elasticity to the non-elastic portion of the substrate. In this particular example, the present invention provides a continuous elastic waistband 32 about a continuous waist border 30, such that waistband 32 does not substantially restrict or diminish the elasticity of elastic side sections 20 and provides a desired elasticity to non-elastic front and back segments 84, 86. The elasticity that can be provided to non-elastic front and back segments 84, 86 can be in the range of between 0 percent to the maximum elasticity of the material of which a joined continuous waistband 32 is made.

Following is one example of a selectively elasticized continuous waistborder 30. With reference to FIGS. 4 and 5, front and back waistborder sections 42, 46 define continuous waistborder 30 (FIG. 1), and have front and back waistband members 64, 66 suitably joined thereto, respectively. Since the joining of front waistband member 64 to front waistborder section 42 can be identical to the joining of back waistband member 66 to back waistborder section 46, a description only of the former will be given. In this example, each elastic side segment 82 (FIG. 2) has an elasticity of about 180%, i.e., each elastic side segment 82 can be extended 2.8 times its original length. It is desired, in this example, that non-elastic front segment 84 be given an elasticity different from that of elastic side segment 82. In fact, the present invention contemplates that non-elastic front segment 84 ultimately can have an elasticity between 0% to the maximum elasticity of the elastic material chosen for front waistband member 64.

Front waistband member 64 (FIGS. 4, 5) includes side portions 88 and a recoverable front portion 90 therebetween. It is desired that front waistband member 64 be a unitary structure. However, side portions 88 and front portion 90 can be separate structures suitably joined together to form front waistband member 64. Since elastic side segments 82 (FIG. 2) have an elasticity of about 180%, front waistband member 64 is selected and configured, in this example, also to have an elasticity of about 180%. Each side portion 88 in FIG. 4 has a length, as measured along centerline 60 (FIG. 5) of about 50 millimeters, and recoverable front portion 90 has a length of about 90 millimeters.

Front waistborder section 42 in FIG. 4 includes two elastic side segments 82 sandwiching non-elastic front segment 84. Each side segment 82 in FIG. 4 has a length of about 50 millimeters, and front segment 84 has a length of about 150 millimeters. Prior to joining front waistband member 64 to front waistborder section 42, recoverable front portion 90 is elongated about 67%, which results in an extended length of about 150 millimeters. After extending recoverable front portion 90, it is temporarily elastically inhibited such as by, for example, compression, thereby providing front portion 90 with the property of being totally recoverable, i.e., able to return to an elastic condition upon being suitably activated, such as by treating with heat. After front portion 90 has been extended and temporarily elastically inhibited, front waistband member 64 is suitably joined, such as by ultrasonic, heat, or adhesive bonding, to front waistborder section 42, such that front portion 90 is joined to front segment 84.

In a similar manner, back waistband member 66 is joined to back waistborder section 46. Thereafter, disposable absorbent garment 10 is folded along a fold line generally parallel to transverse centerline 60, and front outer edges 50 (FIG. 5) are suitably bonded to back outer edges 58 to form seams 22. Garment 10 is then treated, such as with heat, in order to activate temporarily elastically inhibited front portion 90 and back portion 92. Upon total recovery, front portion 90 will gather non-elastic front segment 84 and back portion 92 will gather non-elastic back segment 86. Depending upon the selection of materials for front and back waistborder sections 42, 46, and front and back waistband members 64, 66, front segment 84 and front portion 90, when joined together, can have an elasticity between about 30% to about 60%.

It will be appreciated that the elasticity about waist opening 24 of garment 10 (FIG. 1) depends on various factors, such as the types of materials of which waistband 32 and waistborder 30 are comprised, their elastic characteristics, and the like. Thus, continuous waistband 32 will need to be carefully designed and constructed, as to materials and elasticity, so that once it is suitably joined to continuous waistborder 30, front and back segments 84, 86 will be given the desired elasticity. The same care and attention should be given to other products and items made in accordance with the present invention.

Figure 6:
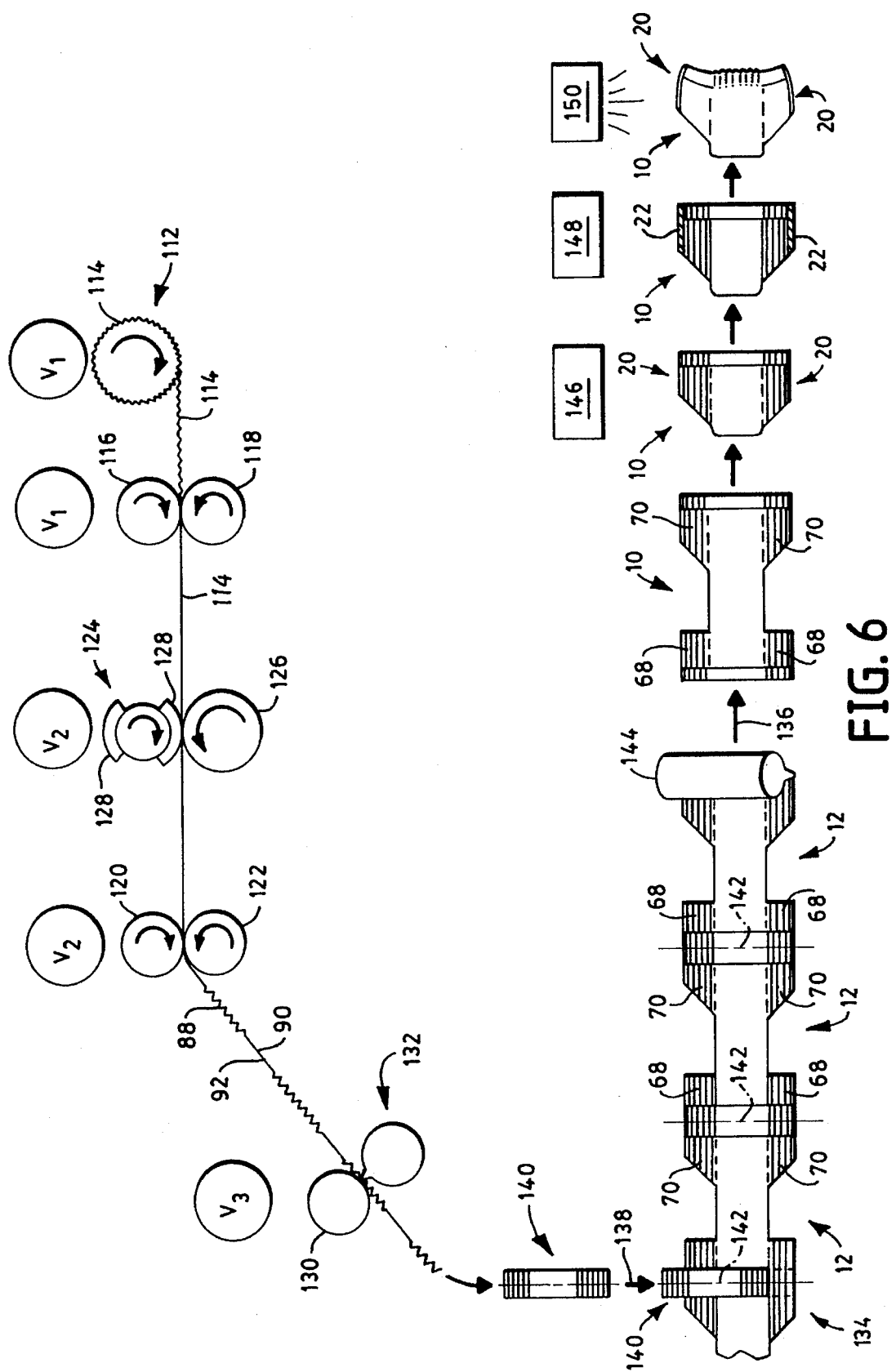
FIG. 6 illustrates schematically one method of the present invention.

Referring now to FIG. 6, there is schematically illustrated one process operated in accordance with the principles of the present invention. Supply roll 112 supplies a continuous length of an elastic material or a composite elastic material 114 between a pair of nip rolls 116, 118. Supply roll 112 and nip rolls 116, 118 have the same rotational velocity $V_1$. Between supply roll 112 and nip rolls 116, 118, composite elastic material 114 is in a substantially untensioned state. Composite elastic material 114 is delivered between chill roll 120 and idler roll 122, both of which have a rotational velocity $V_2$ that is greater than $V_1$. Thus, between nip rolls 116, 118, and chill roll 120 and idler roll 122, composite elastic material 114 is in an extended, tensioned state due to the described difference in rotational velocities. By varying the rotational velocity of nip rolls 116, 118 and/or chill roll 120/idler roll 122, the length of and tension on composite elastic material 114 can be selectively controlled or varied. Between nip rolls 116, 118 and chill roll 120, idler roll 122 are pressure roll 124 and idler roll 126, which have a rotational velocity $V_2$, the same as chill roll 120 and idler roll 122. Pressure roll 124 includes a pair of pressure sleeves 128 for selectively inhibiting temporarily, by compression, those portions of composite elastic material 114 that pass between a pressure sleeve 128 and idler roll 126.

Chill roll 120 may be used to enhance the treatment of composite elastic material 114. For example, the temporarily inhibited portion of composite elastic material 114 is chilled when it contacts the surface of chill roll 120, which causes an increase in the period of time that the portion is inhibited. Temporary inhibition may be prolonged, for example, from about 2 to about 5 seconds by contact with chill roll 120 for a period of about ¼ to about 1 ½ seconds. Greater contact times will result in longer periods of inhibition. Chill roll 120 is maintained at a temperature lower than the temperature of the temporarily inhibited portion of composite elastic material 114. Temperatures from about 60 degrees Fahrenheit to about 33 degrees Fahrenheit have been found practical, although lower temperatures may be used.

After chill roll 120 and idler roll 122, composite elastic material 114 is delivered to anvil roll 130 and knife roll 132, which have a rotational velocity $V_3$ that is less than $V_2$. Because of this difference in rotational velocities between chill roll 120 and knife roll 132, composite elastic material 114 will be in a substantially untensioned state. This allows the portion of composite elastic material 114 that was not temporarily inhibited to contract, thereby forming those portions that correspond to elastic side portions 88 of waistband 32 (FIG. 2). Similarly, the temporarily inhibited portion corresponds to front and back portions 90, 92 of waistband 32.

As will be explained hereafter, composite elastic material 114 has a width that is twice the width of waistband 32, and has an elasticity of about 180%. Between rolls 116, 118 and rolls 120, 122, composite elastic material 114 is extended to an elongation of about 67%, and at this elongation passes between pressure roll 124 and idler roll 126 to be compressed by a pressure sleeve 128 and idler roll 126, thereby having its elasticity selectively inhibited temporarily. Between rolls 120, 122, and rolls 130, 132, the uncompressed portions have substantially recovered to their original elasticity of about 180%.

A continuous partially elastic substrate 134 is continuously moving in a first direction of travel, as illustrated by arrow 136. Substrate 134 can be any type of partially elastic material for manufacturing various products, such as those earlier described. In this specific example, substrate 134 comprises a continuous length of partially finished elastic pant bodies 12, in which each includes front and back elastic side members 68, 70 that are extensible in a direction generally transverse to the direction of arrow 136.

After being cut into select lengths by knife roll 132 and anvil roll 130, individual lengths 140 of composite elastic material 114 are delivered in a direction, illustrated by arrow 138, generally transverse to the first direction 136 of travel of continuous partially elastic substrate 134. One method and apparatus that can be used to accomplish this is described in U.S. Pat. No. 4,608,115, issued Aug. 26, 1986, to Schroth et al., which is incorporated by reference herein.

Each individual length 140 of composite elastic material 114 is suitably intermittently joined, such as by ultrasonic, heat, or adhesive point bonding to continuous partially elastic substrate 134 at selected locations thereof. The selected locations correspond to the transverse line along which continuous partially elastic substrate 134 will be cut in order to produce individual disposable absorbent garments 10. The cut line 142 corresponds to front edge 44 (FIG. 5) and back edge 48 of two garments 10.

After an individual length 140 of composite elastic material 114 has been joined to continuous partially elastic substrate 134, substrate 134 is delivered to a cutting station 144, at which substrate 134 is cut along cut line 142. The cutting station 144 can be any suitable apparatus known in the art.

This cutting of substrate 134 results in individual, partially finished disposable absorbent garments 10. These garments 10 are then delivered to a folding and aligning station 146 where garment 10 will be folded with its outer edges 50, 58 (FIG. 5) aligned for subsequent bonding. One apparatus and method for aligning outer edges 50, 58 is described in U.S. No. 5,046,272 issued Sep. 10, 1991, to Vogt et al., which is incorporated by reference herein.

Thereafter, a folded and aligned garment 10 proceeds to bonding station 148 where the aligned outer edges 50, 58 are bonded to form seams 22. The bonding can be accomplished in any suitable manner, such as by rotary ultrasonic bonding. Finally, the bonded garment 10 proceeds to activation station 150 where temporarily inhibited front and back portions 90, 92 are activated, by treating with heat for example, to recover their elasticity.

In the finished disposable absorbent garment 10, elastic side portions 88 of waistband 32 have, in this example, substantially the same elasticity as elastic side sections 20, while front and back portions 90, 92 provide an elasticity in the range of about 30% to about 60% to non-elastic front and back segments 84, 86. The amount of elasticity of back segments 84, 86 will depend on several factors, such as the materials used and manufacturing operating conditions.

Figure 7:
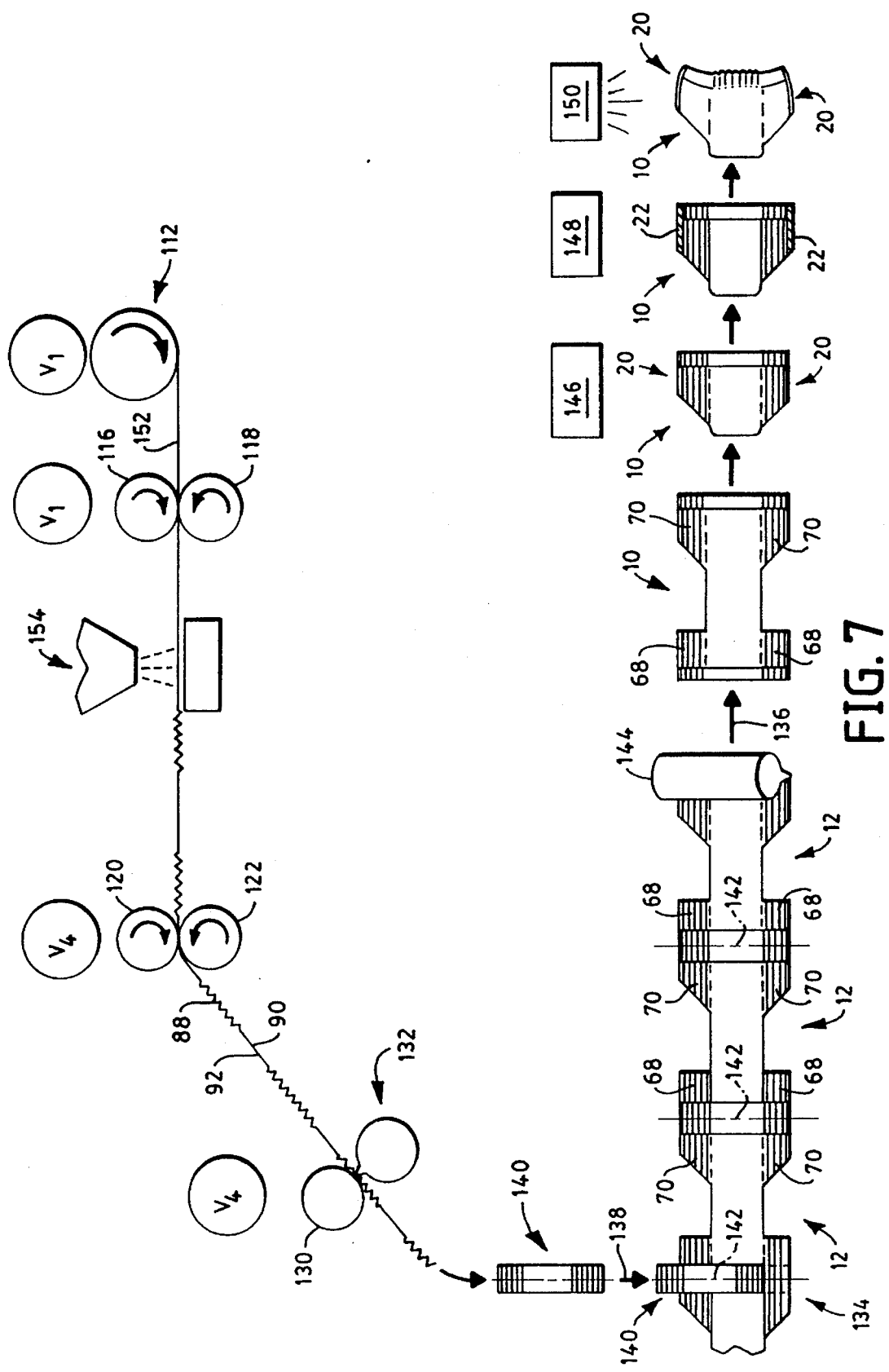
FIG. 7 illustrates schematically a modification of the method in FIG. 6.

FIG. 7 illustrates a modification to the method illustrated in FIG. 6. Supply roll 112 provides a continuous supply of heat-elasticizable material 152 to nip rolls 116, 118. Supply roll 112 and nip rolls 116, 118 have a rotational velocity $V_1$. Material 152 is conveyed to roll 120', which may or may not be chilled, and idler roll 122, which have a rotational velocity $V_4$ less than $V_1$. Activation station 154 is positioned between rolls 116, 118 and rolls 120, 122, and directs a stimulus, for example, heat radiation, against heat-elasticizable material 152 to elastically activate selected portions thereof. As these portions are elastically activated, they "shrink" in length and become elastic. Thus, the rotational velocity of rolls 120, 122 needs to be less than the rotational velocity of rolls 112, 116, 118. By selectively controlling activation station 154, material 152 is provided with "activated" elastic portions of desired length, as well as "non-activated" non-elastic portions of desired length. The "activated" portions correspond to elastic side portions 88 (FIG. 2), and the "non-activated" portions correspond to front and back portions 90, 92 of waistband 32. The result is a continuously moving material 152 that includes alternating elastic and non-elastic portions. Material 152 then may be selectively cut to provide individual lengths 140 of an elastic material. Thereafter, the individual lengths 140 of elastic material can be suitably joined to substrate 134 in a manner similar to that described above with reference to the process represented by FIG. 6. Substrate 134 can then be cut at station 144, folded and aligned at station 146, bonded at station 148, and activated at station 150.

Although the above description of a process of the present invention was made in relation to a disposable training pant, the present invention can be used to make other types of products or items where it is desired to join an elastic material to a continuously moving, partially elastic substrate. Thus, while this invention has been described as having a preferred embodiment, it will be understood that it is capable of further modifications. This application is therefore intended to cover any variations, equivalents, uses, or adaptations of the invention following the general principles thereof, and including such departures from the present disclosure as come or may come within known or customary practice in the art to which this invention pertains and fall within the limits of the appended claims.

What is claimed is:

1. A method of joining a plurality of elastic bands to a continuously moving, partially elastic substrate, comprising the steps of:

continuously moving in a first direction a substrate including a plurality of non-elastic segments and a plurality of elastic segments that are extensible in a second direction different from the first direction, providing a supply of an elastic band, tensioning the elastic band, temporarily inhibiting portions of the tensioned elastic band, cutting the elastic band into individual elastic bands so that each individual elastic band includes at least one temporarily inhibited portion and at least one elastic portion, sequentially orienting each individual elastic band so that it is extensible in substantially the same direction as the elastic segments of the continuously moving substrate, positioning each individual elastic band over the continuously moving substrate so that each elastic portion of the band is over one of the elastic segments of the substrate, and each temporarily inhibited portion of the band is over one of the non-elastic segments of the substrate, and joining each individual elastic band to the continuously moving substrate.

2. The method of claim 1 further comprising the steps of cutting the continuously moving substrate into a plurality of individual substrates after the step of joining each individual elastic band to the continuously moving substrate, and then folding each individual substrate along a fold line.

3. The method of claim 2 further comprising the step of bonding outer edges of each folded substrate to form a waist opening and a pair of leg openings.

4. The method of claim 3 further comprising the step of activating the temporarily inhibited portion of each bonded substrate to gather the non-elastic segment.

5. The method of claim 1 wherein the at least one elastic portion of each elastic band has an elasticity substantially the same as an elasticity of the elastic segments of the substrate.

6. The method of claim 1 wherein the step of temporarily inhibiting includes temporarily inhibiting the portions of the tensioned elastic band at an elasticity different from an elasticity of the elastic segments of the substrate.

7. The method of claim 6 wherein the elasticity of the temporarily inhibited portions are less than the elasticity of the elastic segments, of the substrate.

8. The method of claim 1 wherein the extensible direction of the elastic segments is generally transverse to the first direction.

9. The method of claim 1 wherein the substrate is a composite structure.

10. The method of claim 1 further comprising the step of increasing the period of time that the temporarily inhibited portions are inhibited.

11. A method of joining a plurality of elastic bands to a continuously moving, partially elastic composite structure, comprising the steps of:

continuously moving in a first direction a composite structure including a continuous topsheet, a continuous backsheet, a plurality of spaced apart absorbent structures between the continuous topsheet and the continuous backsheet, and a plurality of spaced apart elastic side members on opposite sides of the continuous backsheet and being extensible in a second direction different from the first direction, providing a supply of an elastic band, tensioning the elastic band, temporarily inhibiting portions of the tensioned elastic band, cutting the elastic band into individual elastic bands so that each individual elastic band includes a pair of elastic portions and a temporarily inhibited portion therebetween, sequentially orienting each individual elastic band so that it is extensible in substantially the same direction as the elastic side members of the continuously moving composite structure, positioning each individual elastic band over the continuously moving composite structure so that the temporarily inhibited portion of the band is over the backsheet, and the pair of elastic portions are over a respective pair of opposite spaced apart elastic side members, and joining each individual elastic band to the continuously moving composite structure.

12. The method of claim 11 further comprising the steps of cutting the continuously moving composite structure into a plurality of individual composite structures after the step of joining each individual elastic band to the continuously moving composite structure, and then folding each individual composite structure along a fold line.

13. The method of claim 12 further comprising the step of bonding outer edges of each folded composite structure to form a waist opening and a pair of leg openings.

14. The method of claim 13 further comprising the step of activating the temporarily inhibited portion of each bonded composite structure.

15. The method of claim 14 wherein the elastic portions of the band have an elasticity substantially the same as an elasticity of the elastic side members.

16. The method of claim 14 wherein the step of temporarily inhibiting includes temporarily inhibiting portions of the elastic band at an elasticity different from an elasticity of the elastic side members.

17. The method of claim 14 wherein the extensible direction of the elastic side members is generally transverse to the first direction.

18. The method of claim 14 wherein the topsheet is a non-woven web, and the backsheet includes a film.

19. The method of claim 11 further comprising the step of increasing the period of time that the temporarily inhibited portions are inhibited.

* * * * *